United States Patent [19]

Yeakel

[11] Patent Number: 5,022,392
[45] Date of Patent: Jun. 11, 1991

[54] APPARATUS FOR SECRETION DEFLECTION DURING INTUBATION

[76] Inventor: Joseph D. Yeakel, 3954 Saint Edmund Ave., NW., Canton, Ohio 44718

[21] Appl. No.: 593,264

[22] Filed: Oct. 1, 1990

Related U.S. Application Data

[63] Continuation of Ser. No. 276,022, Nov. 22, 1988, abandoned.

[51] Int. Cl.$^5$ .................................... A61M 16/00
[52] U.S. Cl. ........................ 128/202.28; 128/202.29
[58] Field of Search ............... 128/202.28, 202.29, 128/204.18, 203.11, 205.25, 207.14, 207.15, 207.16, 207.17, 200.26, 206.12, 206.15, 206.21, 206.22, 206.24, 206.29

[56] References Cited

U.S. PATENT DOCUMENTS

| | | | |
|---|---|---|---|
| 146,730 | 1/1874 | Vickers | 128/207.14 |
| 1,835,757 | 12/1931 | Burchett | 128/207.17 |
| 2,857,911 | 10/1958 | Bennett | 128/207.14 |
| 3,037,501 | 6/1962 | Miller | 128/206.29 |
| 3,809,079 | 5/1974 | Buttaravoli | 128/206.24 |
| 3,874,377 | 4/1975 | Davidson | 128/207.15 |
| 3,905,361 | 9/1975 | Hewson | 128/207.15 |
| 3,987,798 | 10/1976 | McGinnis | 128/207.15 |
| 4,009,720 | 3/1977 | Crandal | 128/207.15 |
| 4,030,493 | 6/1977 | Walters et al. | 128/207.14 |
| 4,222,378 | 9/1980 | Mahoney | 128/207.14 |
| 4,270,529 | 6/1981 | Muto | 128/207.17 |
| 4,325,366 | 4/1982 | Tabor | 128/207.16 |
| 4,360,017 | 11/1982 | Barlett | 128/207.14 |
| 4,497,318 | 2/1985 | Donmichael | 128/207.15 |
| 4,580,556 | 4/1986 | Kondur | 128/206.29 |
| 4,593,689 | 6/1986 | White | 128/207.15 |
| 4,649,913 | 3/1987 | Watson | 128/207.14 |
| 4,697,587 | 10/1987 | Marinkovich | 128/207.16 |
| 4,811,730 | 3/1989 | Milano | 128/202.28 |

FOREIGN PATENT DOCUMENTS

| | | | |
|---|---|---|---|
| 117979 | 8/1918 | United Kingdom | 128/206.22 |
| 889130 | 2/1962 | United Kingdom | 128/206.29 |
| 2056285 | 3/1981 | United Kingdom | 128/207.15 |

Primary Examiner—Edgar S. Burr
Assistant Examiner—Moshe I. Cohen
Attorney, Agent, or Firm—Renner, Kenner, Greive, Bobak Taylor & Weber

[57] ABSTRACT

An umbrella for protecting health provides from the ejection of contaminants from a patient during intubation. The umbrella includes a tubular adapter in axial alignment with a hemispherical shroud, secured thereto by means of a number of radially extending struts. A gutter is circumferentially maintained about an open bottom edge of the shroud. A piercable membrane or removable cap is maintained at a top portion of the shroud and in alignment with the tubular adapter for receipt of a stylet or other medical implement, if required.

8 Claims, 1 Drawing Sheet

APPARATUS FOR SECRETION DEFLECTION DURING INTUBATION

This is a continuation of U.S. application Ser. No. 276,022, filed Nov. 25, 1988 now abandoned.

TECHNICAL FIELD

The invention herein resides in the art of emergency and surgical apparatus and, more particularly, to apparatus used for introducing air or oxygen into the lungs for artificial respiration.

BACKGROUND ART

The primary and paramount skill required for the care of a patient or victim is the establishment and protection of an appropriate airway, an unobstructed pathway to permit passage of gaseous fluid such as air or oxygen into the lungs. Many techniques and devices have been developed to assist in this process. In the hands of the skilled, an endotracheal tube provides the most reliable passage way to the lungs, permitting both enhanced oxygen delivery (respiration) as well as a means to assist the patient with movement of air (ventilation). Many other devices have been developed to secure the airway, the differences among them primarily relating to ease of insertion and level of required skill. Such known devices are typically used by emergency medical field personnel. Once in place, the prior art devices serve a second critical function by preventing entry into the lungs of other materials such as stomach contents, blood, debris, and the like. With the tube in place, the patient's lungs are protected. However, there is little to protect the health care personnel from contamination from the same substances which may include dangerous and infectious material such as viruses and the like.

Common to most known devices is the process of insertion of an object into the pharyngeal cavity through the nose or mouth. Another method is entry through an incision in the neck created by a cricothyroidotomy. The resultant path is directly into the trachea. Predictably, the area of insertion is irritated and frequently there is a corresponding gag or cough reflex by the patient. This is particularly true where entry is made through the nose or mouth. The tube being inserted then functions as a conduit to direct any expelled secretions, such as nebulized partials, liquids and solids, into the environment, exposing the personnel involved. Expelled material has been shown to travel radially as far as sixteen feet, exposing all within that region to the same. The process of intubation and securing the airway requires close proximity of the operator's face and that of the patient. If exposed, contamination of the operators mucous membranes (eyes, mouth, and the like) may occur. The material expelled may contain hazardous and even lethal material such as infectious contaminants like hepatitis virus, bacteria, and the AIDS virus, as well as toxic materials such as cyanide, radioactive substances and the like.

There is a need for an apparatus to be placed over the exposed and open end of a tube during insertion, thus reducing the operator's risk of exposure to potentially contaminating material. It must not, however, interfere with the intubation process Through U.S. Pat. Nos. 3,905,361; 4,090,518; and 4,231,365, it is known that a face shield may be attached to an airway passage. However, the face shield of each of these prior art references is designed to provide a sealed airway and does not function to prevent secretion exposure to health personnel. In each of these devices, an opening exists in the face mask, available for passage of expelled material.

There is a need in the art for a device which may be temporarily attached to an appropriate implement being used to secure the airway, such device serving to deflect and collect expelled secretions during the insertion phase. Once the tube is secured by established procedures, the device should be capable of being easily removed, safely discarded, and replaced with whatever apparatus is needed, such as a ventilator connection or an ambu bag.

When an endotracheal tube is inserted into the patient, the health care provider often uses a malleable stylet in the bore of the tube. With the stylet in place, the otherwise soft flexible tube can be temporarily molded so as to assist the placement of the tube into the trachea. It is most desirable that a device to deflect and collect expelled secretions should be so designed as to permit use of the stylet.

Additionally, there is a temporary but critical period of time during the intubation process during which no supplemental oxygen can be provided. Accordingly, it is most designable that any device employed for deflecting and collecting expelled secretions include a port for attachment to a source of supplemental oxygen. Of course, this modification would only be of use for the patient who is still breathing during the intubation process.

DISCLOSURE OF INVENTION

In light of the foregoing, it is a first aspect of the invention to provide an apparatus for secretion deflection during intubation which protects health care personnel from exposure to contaminating substances which may be expelled during the intubation procedure.

It is another aspect of the invention to provide an apparatus for secretion deflection during intubation which will not hinder air flow while in use, and which may be readily discarded after the airway is secured.

A further aspect of the invention is the provision of an apparatus for secretion deflection during intubation which may accommodate the use of a stylet during the airway securing process.

Yet another aspect of the invention is the provision of an apparatus for secretion deflection during intubation which permits oxygenation of inspired air during the securing process.

Still a further aspect of the invention is the provision of an apparatus for secretion deflection during intubation which permits use of a suction catheter to remove pulmonary secretions.

Another aspect of the invention is the provision of an apparatus for secretion deflection during intubation which includes means to collect expelled material, decreasing exposure to the health care personnel while permitting the retention of such material for subsequent analysis.

The foregoing and other aspects of the invention which will become apparent as the detailed description proceeds are achieved by an apparatus for secretion deflection, comprising: a shroud; and a tubular member received by said shroud.

Other aspects of the invention are obtained by an umbrella for secretion deflection, comprising: a tubular member; a generally hemispherical shroud received by said tubular member and in axial alignment therewith;

and a gutter encircling a bottom edge of an open end of said shroud, said gutter extending inwardly of an outer surface of said shroud.

DESCRIPTION OF DRAWINGS

For a complete understanding of the objects, techniques and structure of the invention, reference should be had to the following detailed description and accompanying drawings wherein.

BEST MODE FOR CARRYING OUT THE INVENTION

Figure 1:
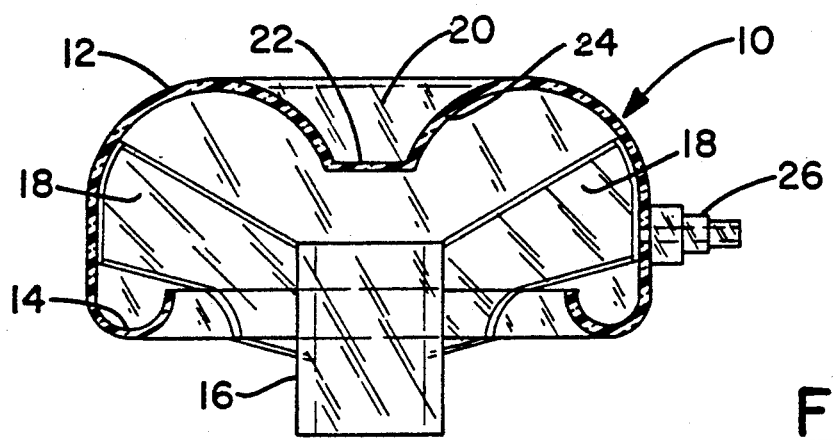
FIG. 1 is a cross-sectional view of a secretion deflection umbrella according to a first embodiment of the invention.

Referring now to the drawings and more particularly FIG. 1, it can be seen that a secretion deflection umbrella according to a first embodiment of the invention is designated generally by the numeral 10. While the umbrella 10 may be devised from any of a number of suitable materials, it is preferred that a clear vinyl plastic be employed such that the device 10 is substantially transparent so as not to block the view of the health care provider in employing the same. The umbrella 10 includes a generally hemispherical shroud 12 which is curled inwardly at an open bottom edge thereof to define a gutter 14 about the lower circumference of the shroud. A tubular member or cylindrical adapter 16 is centrally located with respect to the shroud 12 and in axial alignment therewith. As has become standard in the art, the cylindrical adapter 16 would typically have an inside diameter on the order of 15 mm, although various such diameters may be employed within the concept of the invention. The cylindrical adapter 16 and shroud 12 are maintained in fixed axial alignment by means of a plurality of struts 18 interconnecting the two. While any number of struts might be employed, it is desired that at least three be used to assure stability and integrity of the unit.

The top portion of the shroud 12 is preferably characterized by a conical recess 20 which is axially aligned with the cylindrical adapter 16. As shown, the conical recess 20 is truncated at the bottom thereof, which is characterized by a thin membrane 22. This membrane may be pierced for insertion of a stylet of malleable material to assist in the intubation process in standard fashion.

It will be appreciated that an inner conical surface 24 is provided in alignment with the cylindrical adapter 16 such that the entire inner surface of the shroud 12 is of a curvate nature, contoured from the axis of the tubular adapter 16 to the inwardly turned gutter 14.

As shown, a side port 26 may be provided for connection to a supplemental oxygen source to assist the patient or victim in respiration during the intubation process.

Figure 2:
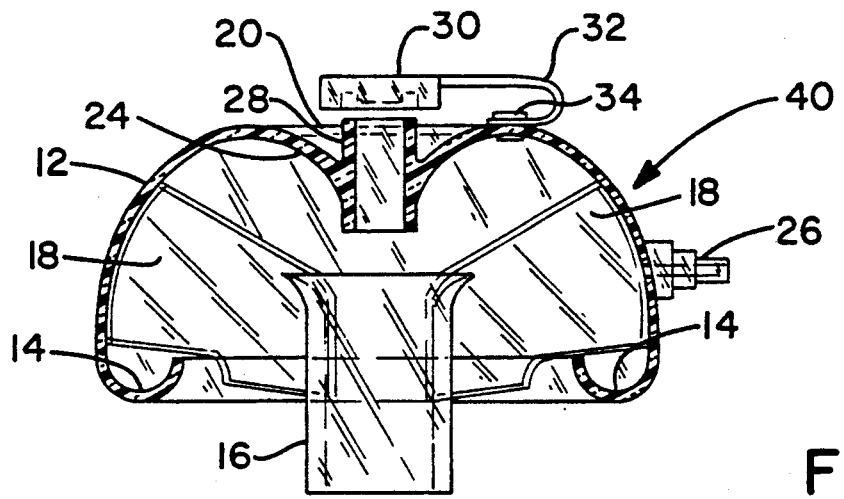
FIG. 2 is a cross-sectional view of a secretion deflection umbrella according to a second embodiment of the invention.

As shown in FIG. 2, a second embodiment of the invention is designated generally by the numeral 40. Elements corresponding to those of the embodiment of FIG. 1 are designated by the same numerals. The primary difference between the two embodiments is the substitution in the umbrella 40 of a top port 28 for the membrane 22. Again, the top port 28 is at the center of the conical recess 20 and in axial alignment with the cylindrical adapter 16. The top port 28 is adapted to be selectively sealed by a cap 30 which is connected to a pin 34 by means of a band 32. If a stylet is to be employed, the cap 30 is simply removed from the top port 28 accommodating entry of the stylet through the port 20 and cylindrical adapter 16.

Figure 3:
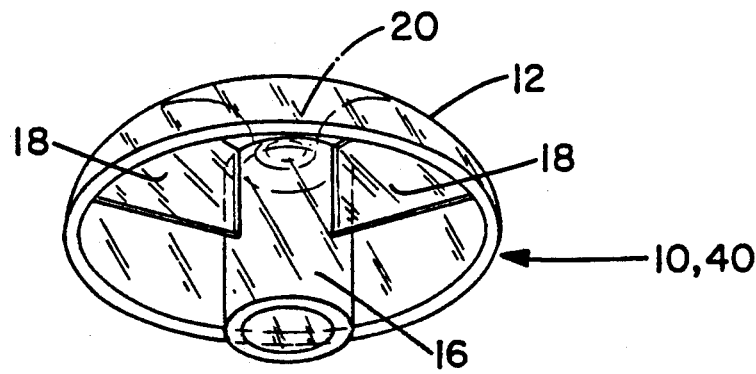
FIG. 3 is a lower isometric view of a deflection umbrella as shown in FIGS. 1 and 2, but absent a collection gutter.

It will be appreciated that the embodiment of FIG. 3 is shown for illustrative purposes and is equally applicable to both of the embodiments 10 and 40.

In use, the umbrella 10, 40 may be attached to the ventilating end of an endotracheal tube prior to insertion into the trachea. As the tube is inserted into the trachea in a manner well known and understood by those skilled in the art, stimulating the same, the umbrella 10, 40 serves to protect the health provider from any expelled material or body secretions which might be forced through the tube by an explosive cough or the like by the patient. If such passage does occur, the inner curvate surface of the shroud 12 allows the excretions or ejections to pass there along and to be retrieved by the circumferential gutter 14. Being so retrieved and retained, the expelled matter may be later analyzed during the health care process.

Once the endotracheal tube is in place, and stimulation of the trachea has terminated such that a violent cough is unlikely, the umbrella 10, 40 may be removed and the endotracheal tube attached to an appropriate ventilator connection, ambu bag, or the like.

It will also be appreciated that the thin membrane 22, when punctured by a stylet, still retains sealed integrity during employment of the device. If a stylet is not required, the membrane 22 is not punctured. In like manner, the cap 30 is only removed from the top port 28 in the event that a stylet is necessary. The top port 28 would typically be of a diameter sufficient to receive the stylet in close tolerance, minimizing any open passage therebetween. It will also be understood by those skilled in the art that the membrane 22 or port 28 may be used to provide access of suction tubing, fiberoptic laryngscope, or other appropriate tools for required medical treatment.

It will further be appreciated that the umbrella 10, 40 is of a disposable nature, enhancing its intended purpose of protecting others from body secretion or ejections from patients. The disposability of such devices is further enhanced by the cost effective manner in which such umbrellas may be manufactured and distributed.

Thus it can be seen that the objects of the invention have been satisfied by the structure presented hereinabove. While in accordance with the patent statutes, only the best mode and preferred embodiments of the invention have been presented and described in detail, it is to be understood that the invention is not limited thereto or thereby. Accordingly, for an appreciation of the true scope and breadth of the invention, reference should be had to the following claims.

What is claimed is:

1. Apparatus for secretion deflection, comprising:
   a generally hemispherical shroud having a gutter circumferentially encompassing an open bottom edge thereof; and
   a tubular member having first and second open ends, said first open end being received within said shroud and being axially aligned with said shroud; said tubular member being interconnected with said shroud by struts to hold said tube stationary relative said shroud, and said tubular member not passing completely through said shroud.

2. The apparatus according to claim 1 wherein said gutter extends inwardly from said bottom edge.

3. The apparatus according to claim 1 wherein said shroud has a thin membrane in axial alignment with said tubular member.

4. The apparatus according to claim 3 wherein said shroud has a conical recess in a top portion thereof, said conical recess being in axial alignment with said tubular member.

5. The apparatus according to claim 4 wherein said thin membrane comprises a bottom surface of said conical recess.

6. An umbrella for secretion deflection, comprising:
a tubular member by means of a plurality of struts to hold said tube stationary relative said shroud;
a generally hemispherical shroud received by said tubular member and in axial alignment therewith, said tubular member not passing completely through said shroud and having an open end within said shroud; said shroud having a conical recess therein in axial alignment with said tubular member, said conical recess being truncated at a bottom portion thereof by a thin membrane; and
a gutter encircling a bottom edge of an open end of said shroud, said gutter extending inwardly of an outer surface of said shroud.

7. The umbrella as recited in claim 6 wherein said shroud has a port in a top surface thereof in axial alignment with said tubular member, said port adapted for selected closure with a cap.

8. The umbrella as recited in claim 6 wherein said tubular member is open at each of two opposite ends thereof.

* * * * *